(12) United States Patent
Lu

(10) Patent No.: US 7,306,458 B1
(45) Date of Patent: Dec. 11, 2007

(54) ADJUSTABLE ORTHODONTIC BRACKET

(76) Inventor: Yu-Hua Lu, 2F., No. 313, Sec. 4 Sin-Yi Road, Taipei (TW)

( * ) Notice: Subject to any disclaimer, the term of this patent is extended or adjusted under 35 U.S.C. 154(b) by 0 days.

(21) Appl. No.: 11/457,618

(22) Filed: Jul. 14, 2006

(51) Int. Cl.
*A61C 3/00* (2006.01)

(52) U.S. Cl. ............................................. 433/16; 433/9

(58) Field of Classification Search ................ 433/8, 433/9, 10, 12, 16
See application file for complete search history.

(56) References Cited

U.S. PATENT DOCUMENTS

| | | | | |
|---|---|---|---|---|
| 2,379,011 A | * | 6/1945 | Laskin | 433/16 |
| 3,423,833 A | * | 1/1969 | Pearlman | 433/16 |
| 4,107,844 A | * | 8/1978 | Kurz | 433/9 |
| 4,139,945 A | * | 2/1979 | DiGiulio | 433/16 |
| 4,243,387 A | * | 1/1981 | Prins | 433/16 |
| 4,597,739 A | * | 7/1986 | Rosenberg | 433/16 |
| 4,676,746 A | * | 6/1987 | Klapper | 433/16 |
| 4,867,678 A | * | 9/1989 | Parker | 433/8 |

* cited by examiner

*Primary Examiner*—Ralph A. Lewis
(74) *Attorney, Agent, or Firm*—WPAT, PC; Justin I. King

(57) ABSTRACT

This invention provides an adjustable orthodontic bracket. The adjustable orthodontic bracket includes an orthodontic arch wire slot/tube and fixing part, an adjustable part, and a tooth surface fixing part. The orthodontic arch wire slot and fixing part is used to fix one or several orthodontic arch wire(s). The adjustable part is fixed under the orthodontic arch wire slot/tube and fixing part and provides a structure allowing the orthodontic arch wire slot/tube and fixing part to be turned around and fixed, and thereby the orthodontic arch wire slot/tube and fixing part is able to generate a stress to teeth for orthodontic treatment through turning itself around to pull and drag the orthodontic arch wire(s). The tooth surface fixing part is used to fix the adjustable part on tooth surface.

8 Claims, 5 Drawing Sheets

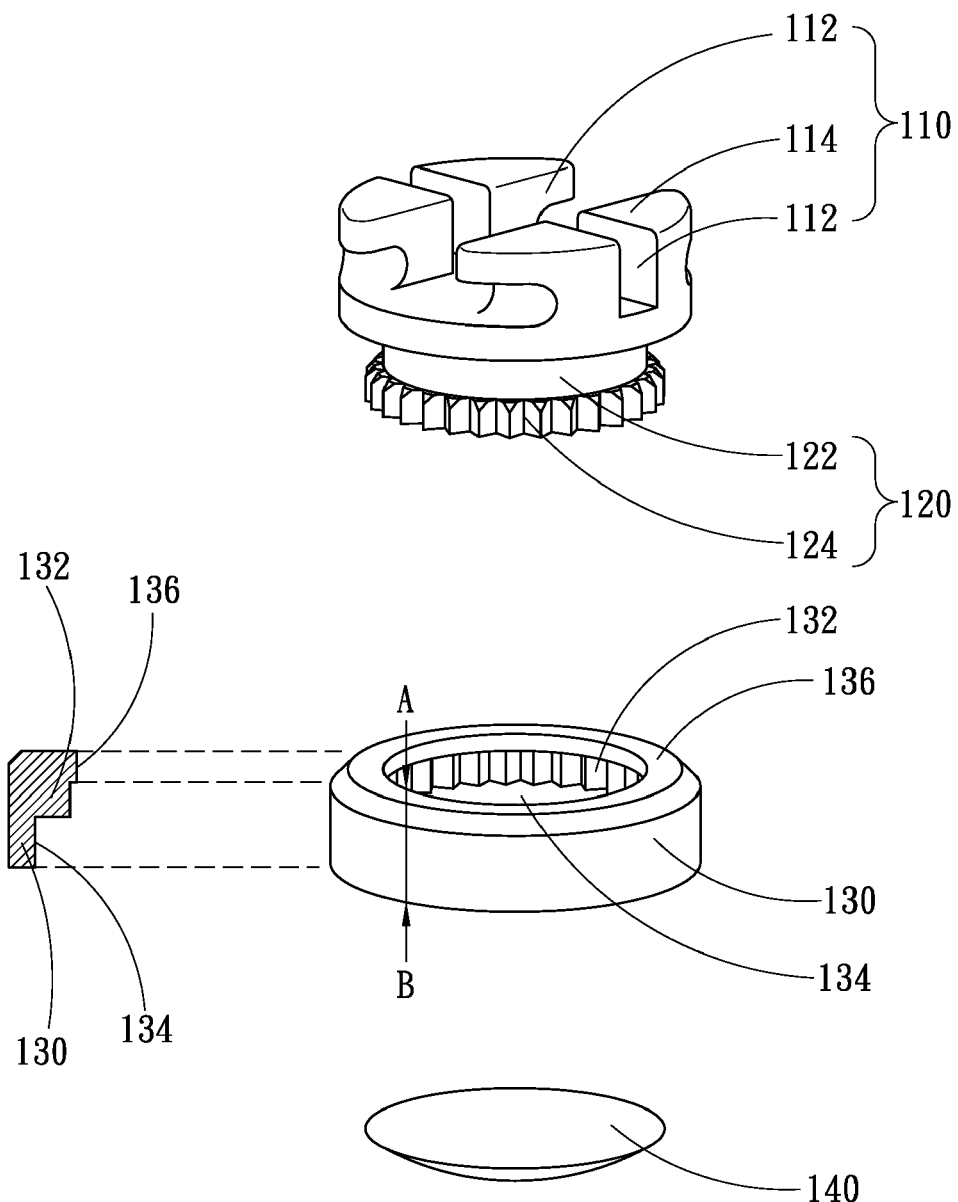
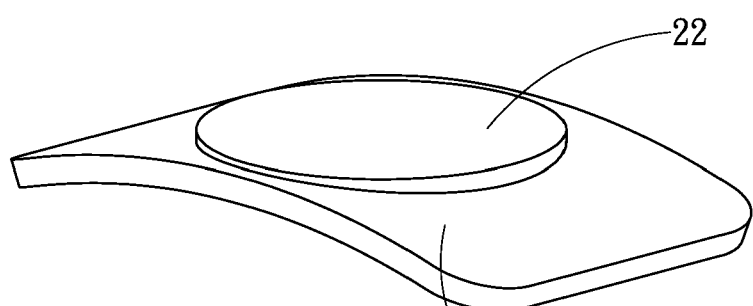

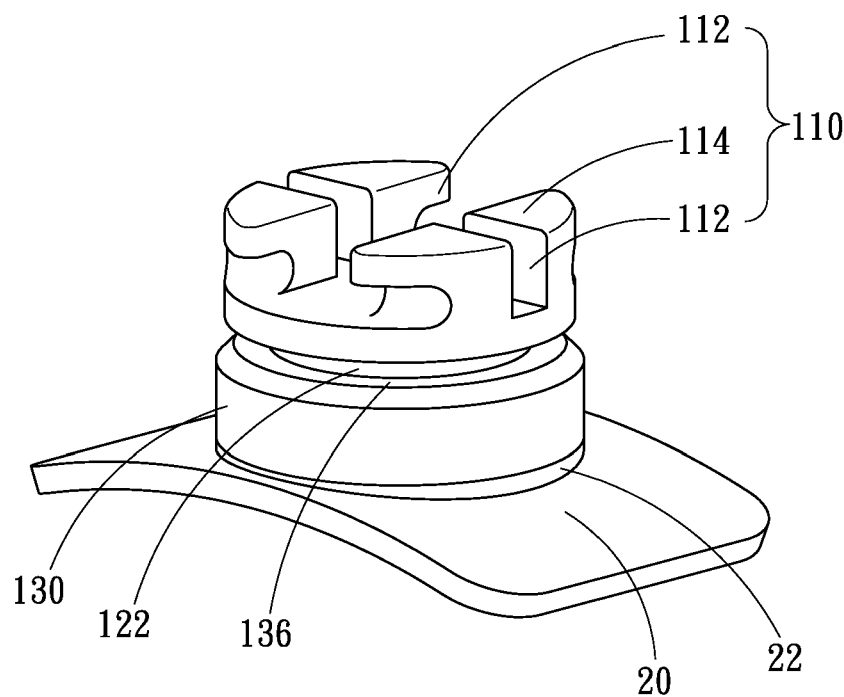
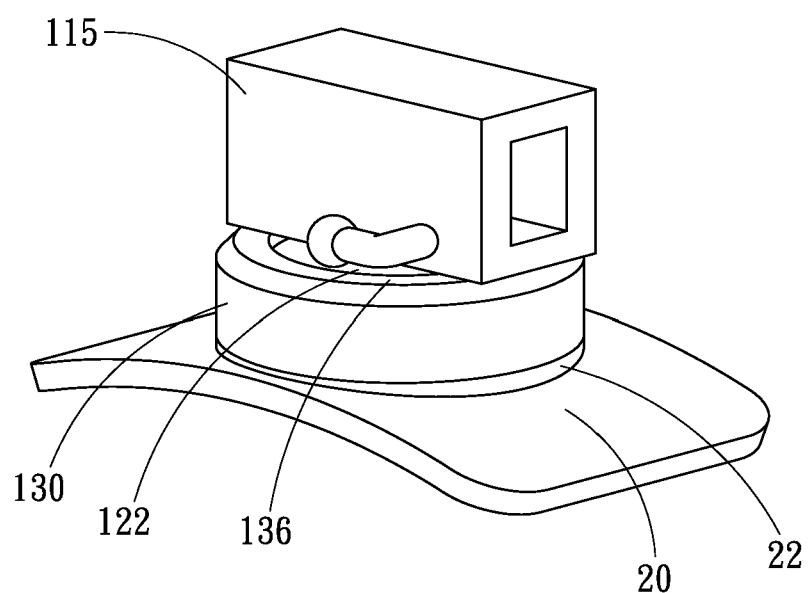
FIG. 3A

ADJUSTABLE ORTHODONTIC BRACKET

BACKGROUND OF THE INVENTION

1. Field of the Invention

This invention generally relates to an orthodontic appliance, and more particularly, to an adjustable bracket for orthodontics.

2. Description of the Prior Art

For the clinic tasks in orthodontics, the orthodontic processes for uprighting tipping teeth or making teeth tilting for some purpose or technique have the highest percentage, and these tasks also spend a lot of clinic time, especially, during the middle stage, later stage of the orthodontic treatment or the finishing stage. The well-known brackets for uprighting the irregular teeth or the horizontal wisdom tooth are not easy to engage the orthodontic arch wire(s) (while the tipping angle is between 30-90 degrees, the tooth is not easy to be or unable to be upright at once), even unable to install. Moreover, during the primary stage limited by the irregular teeth, if the orthodontic arch wire is too thin or too soft, the orthodontic arch wire could have the problems of easily loosing, lacking force, and no self-supporting. These problems delay the rate of the progress of the orthodontic treatment. The well-known orthodontic appliances also make teeth receive the force disproportionately, that is, the optimal force is not easy to be achieved. However, the disproportionate force and direction could make teeth hurt and make the orthodontic arch wire fatigue in elasticity and even snap. In addition, the bonding positions of the brackets must be accurate. As to those brackets with inaccurate position, they must be removed, re-bonded, or be recovered through bending the orthodontic arch wire, that is, this takes a lot of clinic time and requires practiced clinic skill, and further, the orthodontic arch wire bending in the orthodontic treatment requires various materials and various types of orthodontic arch wires. Still, the worst drawbacks of the well-known brackets are that they cannot meet the particular needs and are difficult to be fine adjusted. Explicitly, the finishing stage is not easy to be finished, and this process must take a lot of clinic time (30-60 minutes for each visit) and delays the time of debond, such as one year of orthodontic treatment being delayed to one-half and two years, even to the unforeseeable future.

In view of the drawbacks mentioned with the orthodontic bracket in the prior art, there is a continued need to develop a new and improved orthodontic bracket that overcomes the disadvantages associated with the bracket in the prior art. The advantages of this invention are that it solves the problems mentioned above.

SUMMARY OF THE INVENTION

In accordance with the present invention, an adjustable orthodontic bracket substantially obviates one or more of the problems resulted from the limitations and disadvantages of the prior art mentioned in the background.

This invention provides an adjustable orthodontic bracket. The adjustable orthodontic bracket includes an orthodontic arch wire slot/tube and fixing part, an adjustable part, and a tooth surface fixing part. The orthodontic arch wire slot and fixing part with built-in three dimension angle slot(s) is used to house and fix one or more than one orthodontic arch wires. The forms of the orthodontic arch wire slot and fixing part could be a slot and four-talon, liftable cover, or one or a plurality of tube structures. The adjustable part is fixed under the orthodontic arch wire slot and fixing part and gives a structure allowing the orthodontic arch wire slot and fixing part to be turned around and fixed, and thereby the orthodontic arch wire slot and fixing part can generate a stress to teeth for orthodontic treatment by turning itself around to pull and drag the orthodontic arch wire(s). The tooth surface fixing part is used to fix the adjustable part on tooth surface.

This invention provides an adjustable orthodontic bracket. The adjustable orthodontic bracket includes an orthodontic arch wire slot and fixing talon, a male gear ring, a housing, an elastomer, and a tooth surface fixing plank and base plate. The male gear ring is fixed under the orthodontic arch wire slot and fixing talon. The male gear ring has a smooth external ring surface and a male gear structure ring surface under the smooth external ring surface, wherein the diameter of the male gear structure ring surface is bigger than the diameter of the smooth external ring surface. The housing covers the male gear ring. The housing has a female gear structure ring surface and a smooth internal ring surface under the female gear structure ring surface. The diameter of the smooth internal ring surface is bigger than the diameter of the female gear structure ring surface, and the diameter of the female gear structure ring surface is bigger than the diameter of the upper open of the housing. Wherein, the female gear structure ring surface matches the male gear structure ring surface. The elastomer locates inside the housing and under the male gear ring. The tooth surface fixing plank and base plate locates under the elastomer and connects the base of the housing.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 2 shows disassembled parts of one preferred embodiment in accordance with the present invention;

FIG. 3A illustrates two three-dimensional pictures for two preferred embodiments in accordance with the present invention.

DETAILED DESCRIPTION OF THE PREFERRED EMBODIMENTS

Some embodiments of the invention will now be described in greater detail. However, it should be noted that the present invention can be practiced in a wide range of other embodiments besides those explicitly described, and the scope of the present invention is expressly not limited except as specified in the accompanying claims. Moreover, some irrelevant details are not drawn in order to make the illustrations concise and to provide a clear description for easily understanding the present invention.

Figure 1:
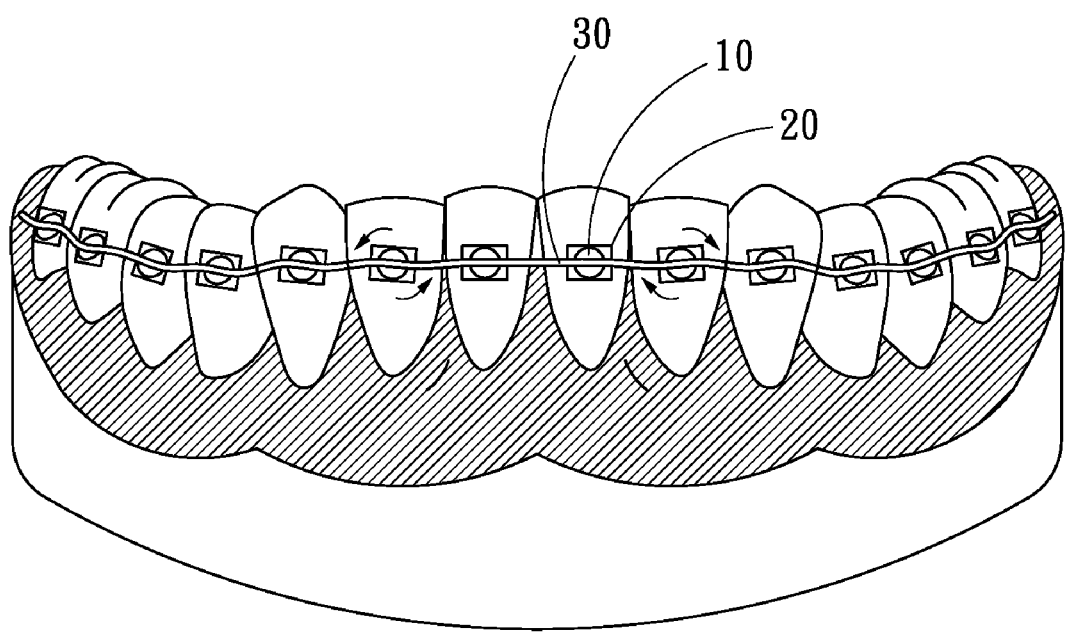
FIG. 1 illustrates teeth with orthodontic appliances.

Referring to FIG. 1, teeth with orthodontic appliances are depicted. A plurality of brackets 10 correspondingly connect with a plurality of tooth surface fixing planks and base plates 20 in order to be fixed on the surfaces of teeth. An orthodontic arch wire 30 connects the brackets 10 to form the orthodontic arch wire to pull the tipping teeth back to normal positions by the pulling force of the orthodontic arch wire 30.

Referring to FIG. 2, disassembled parts for one preferred embodiment in accordance with the present invention are illustrated. A bracket 10 shown in FIG. 1 has an orthodontic arch wire fixing part and an adjustable part. In the present embodiment, the above-mentioned orthodontic arch wire fixing part (having slots 112 and wings 114) could be an orthodontic arch wire slot(s) and fixing talon 110, the adjustable part could be a combination structure with a male gear ring 120 (also called "internal ring" herein), a housing 130 (also called "external ring" herein), and an elastomer 140. Wherein, the male gear ring 120 is fixed under the orthodontic arch wire slot(s) and fixing talon 110. The male gear ring 120 has a smooth external ring surface 122 and a male gear structure ring surface 124 under the smooth external ring surface 122, and herein the diameter of the male gear structure ring surface 124 is bigger than the diameter of the smooth external ring surface 122. The housing 130 covers the male gear ring 120. The housing 130 has a female gear structure ring surface 132 and a smooth internal ring surface 134 under the female gear structure ring surface 132. Wherein, the diameter of the smooth internal ring surface 134 is bigger than the diameter of the female gear structure ring surface 132, and the diameter of the female gear structure ring surface 132 is bigger than the diameter of the upper open 136 of the housing 130. Further, in the present embodiment, the female gear structure ring surface 134 and the male gear structure ring surface 124 can match with each other. The elastomer 140 is located inside the housing 130 and under the male gear ring 120. In the present embodiment, the elastomer 140 could be a sheet-metal with elasticity (such as a disc shape or with several slits) or a rubber sheet, thereby the sheetmetal with elasticity can provide a force to push the male gear ring 120 and the orthodontic arch wire slot(s) and fixing talon 110 up to make the male gear structure ring surface 124 match with the female gear structure ring surface 132 when the orthodontic arch wire slot(s) and fixing talon 110 is not pressed. This makes the orthodontic arch wire slot(s) and fixing talon 110 be unable to turn around. In addition, the bracket in the present invention could further include a tooth surface fixing part used to fix the above-mentioned adjustable part on tooth surface. In the present embodiment, the tooth surface fixing part could be a tooth surface fixing plank 20 and base plate 22 located under the elastomer 140 and connected with the housing 130.

Form another aspect, the above-mentioned orthodontic arch wire slot(s) and fixing part is used to fix one or more than one orthodontic arch wire(s), and the adjustable part is fixed under the orthodontic arch wire slot(s) and fixing part. That is, the adjustable part gives a structure allowing the orthodontic arch wire slot(s) and fixing part to be turned around and fixed. Thereby, the orthodontic arch wire slot(s) and fixing part can generate a particular stress in a particular direction to teeth for orthodontic treatment by turning itself around to pull and drag the orthodontic arch wire. The tooth surface fixing part is utilized to fix the adjustable part on tooth surface. Further, the male gear ring 120 (also called "internal ring" herein) is fixed under the above-mentioned orthodontic arch wire slot(s) and fixing part, and the lower level of the external ring surface of the internal ring has a plurality of male gear structures 124 surrounding with. The housing 130 (also called "external ring" herein) covers the internal ring and the upper level of the internal ring surface of the external ring has a plurality of female gear structures 132 surrounding with. Wherein, the diameter formed by the plurality of female gear structures 132 is smaller than the diameter of the internal ring surface of the external ring, the diameter of the upper open 136 of the external ring is smaller than the diameter formed by the plurality of female gear structures 132, and the plurality of female structures 132 are able to match the plurality of male gear structures 124. Also, the elastomer 140 is located inside the external ring and under the internal ring.

Referring to FIG. 3A, two three-dimensional pictures for two preferred embodiments in accordance with the present invention are illustrated. The difference between the two embodiments is that the upper one shows an orthodontic arch wire slot(s) and fixing talon 110 (having two crossed slots 112 and four wings 114), but the lower one depicts an orthodontic arch wire fixing tube 115. However, regardless of the fixing talon, fixing tube, or other equivalent structure changes, those should be included in the present invention. The orthodontic arch wire slot(s) and fixing talon 110 or the orthodontic arch wire fixing tube 115 is fixed on the male gear ring. The housing 130 covers the male gear ring and connects to and is fixed on the tooth surface fixing plank 20 and base plate 22. Since the diameter of the upper open 136 of the housing 130 is bigger than the diameter of the smooth external ring surface 122 of the male gear ring but smaller than the diameter of the male gear structure ring surface 124 (see FIG. 2), the housing 130 could make a loop for the male gear ring.

Figure 3B:
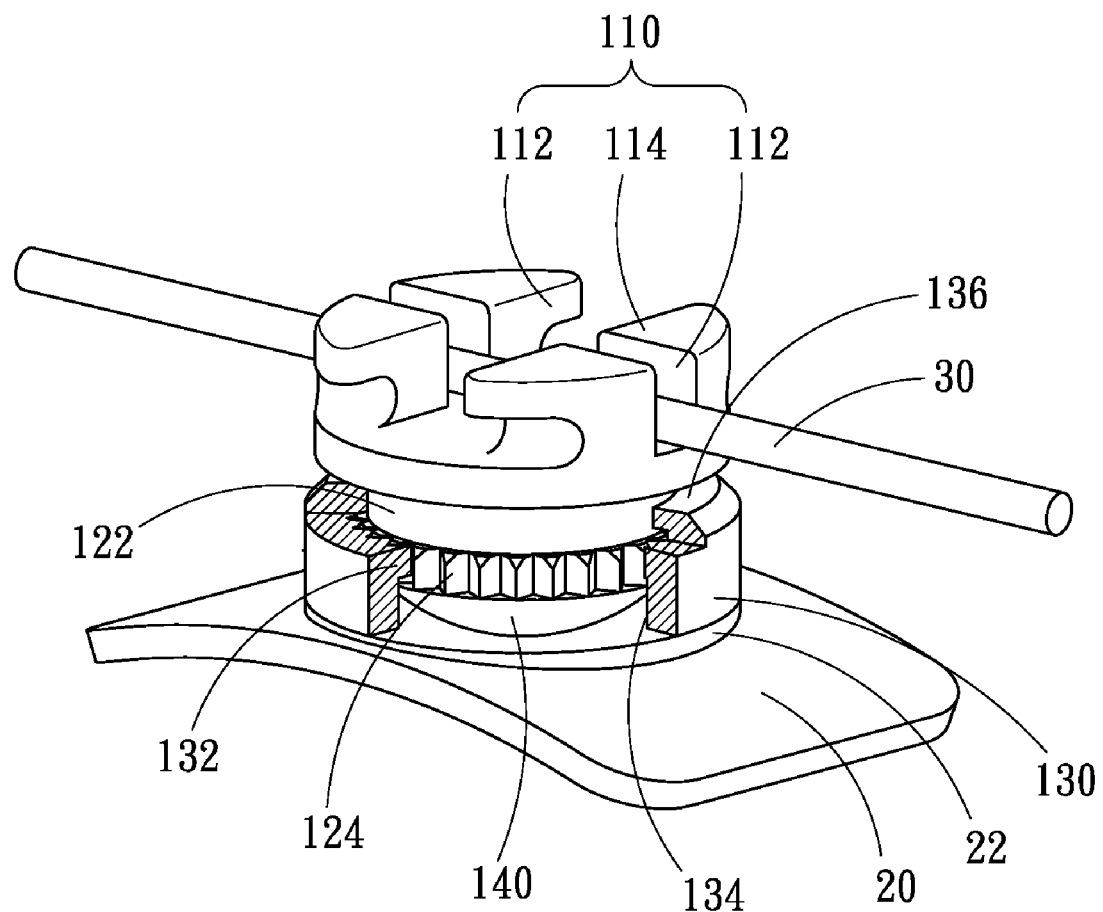
FIGS. 3B-3C illustrate the cutaway views in part for the embodiment shown in FIG. 3A during operation.
Figure 3C:
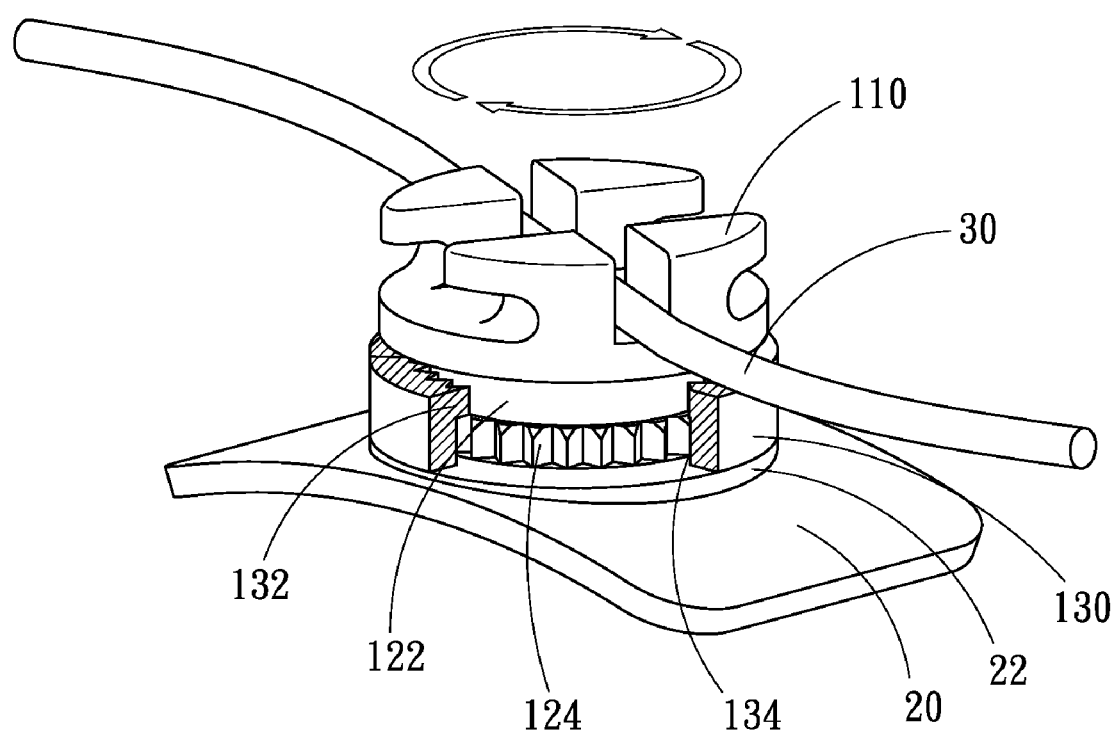

Referring to FIGS. 3B-3C, the cutaway views in part for the embodiment shown in FIG. 3A under operation are illustrated. Wherein, FIG. 3B depicts the structure of the adjustable orthodontic bracket while the orthodontic arch wire slot(s) and fixing talon 110 has no force applied on, and FIG. 3C shows the structure change while the orthodontic arch wire slot(s) and fixing talon 110 is pressed and rotated. The elastomer 140 provides a force to push the male gear ring (the smooth external ring surface 122 and the male gear structure ring surface 124) and the orthodontic arch wire slot(s) and fixing talon 110 up to make the male gear structure ring surface 124 match with the female gear structure ring surface 132 of the housing 130 when the orthodontic arch wire slot(s) and fixing talon 110 is not pressed. This makes the orthodontic arch wire slot(s) and fixing talon 110 fix and be unable to turn around, in the same time, the orthodontic arch wire slot(s) and fixing talon 110 does not provide external force to pull or drag the orthodontic arch wire 30. However, when a force is applied on the orthodontic arch wire slot(s) and fixing talon 110, the orthodontic arch wire slot(s) and fixing talon 110 and the male gear ring (the smooth external ring surface 122 and the male gear structure ring surface 124) compress the elastomer 140. This makes the male gear structure ring surface 124 move backward to the space formed by the smooth internal ring surface 134 of the housing 130, and also makes the smooth external ring surface 122 move backward to the space formed by the female gear structure ring surface 132 of the housing 130. In the meanwhile, the orthodontic arch wire slot(s) and fixing talon 110 can turn around in two ways to pull and drag the orthodontic arch wire 30 to adjust the orthodontic force and direction to achieve an optimal force and direction for individual. As for the tooth surface fixing plank 20 and base plate 20, it not only provides the function for fixing the housing 130 on tooth surface but also offers the function for supporting the elastomer 140, thereby the elastomer 140 is able to push the male gear ring and the orthodontic arch wire slot(s) and fixing talon 110 up by the support of the tooth surface fixing plank 20 and base plate 22. As to the size relations among the diameters of the smooth external ring surface 122, of the male gear structure ring surface 124, of female gear structure ring surface 132, of the smooth internal ring surface 134, and of the upper open 136 of the housing 130 are similar to those described in FIG. 2, it is unnecessary to be repeated herein.

Although specific embodiments have been illustrated and described, it will be obvious to those skilled in the art that various modifications may be made without departing from what is intended to be limited solely by the appended claims.

What is claimed is:

1. An adjustable orthodontic bracket, comprising:
    an orthodontic arch wire fixing member for fixing one or more than one orthodontic arch wires in a position such that a predetermined stress is generated and applied to the tooth to be treated;
    a male gear ring, fixed under said orthodontic arch wire fixing member, said male gear ring having a smooth external ring surface and a male gear structure ring surface under said smooth external ring surface, wherein the diameter of said male gear structure ring surface is bigger than the diameter of said smooth external ring surface;
    a housing, covering said male gear ring, said housing having a female gear structure ring surface and a smooth internal ring surface under said female gear structure ring surface, the diameter of said smooth internal ring surface being bigger than the diameter of said female gear structure ring surface, the diameter of said female gear structure ring surface being bigger than the diameter of the upper open of said housing, wherein said female gear structure ring surface matches said male gear structure ring surface;
    an elastic member, located inside said housing and under said male gear ring for biasing the male gear ring into contact with the female gear ring; and
    a tooth surface attachment plank and base plate, located under said elastic member, said tooth surface attachment plank and base plate connecting with said housing.

2. The adjustable orthodontic bracket according to claim 1, wherein said elastic member comprises a sheetmetal with elasticity.

3. An adjustable orthodontic bracket, comprising:
    an orthodontic arch wire fixing member for fixing one or more than one orthodontic arch wires in a position such that a predetermined stress is generated and applied to the teeth to be treated;
    an adjustable part, fixed under said orthodontic arch wire fixing member, said adjustable part comprising:
        an internal ring, fixed under said orthodontic arch wire fixing member, the lower level of the external ring surface of said internal ring having a plurality of male gear structures surrounding with;
        an external ring, used to cover said internal ring, the upper level of the internal ring surface of said external ring having a plurality of female gear structures surrounding with, wherein the diameter formed by said plurality of female gear structures is smaller than the diameter of the internal ring surface of said external ring, the diameter of the upper open of said external ring is smaller than the diameter formed by said plurality of female gear structures, said plurality of female gear structures and male gear structures are able to match with each other; and
        an elastic member, located inside said external ring and under said internal ring, wherein said adjustable part provides a structure allowing said orthodontic arch wire fixing member to be turned around and fixed, thereby said orthodontic arch wire fixing member is able to generate a stress to teeth for orthodontic treatment through turning itself around to pull and drag said orthodontic arch wire, wherein said adjustable part comprising; and
    a tooth surface fixing part, used to fix said adjustable part on tooth surface.

4. The adjustable orthodontic bracket according to claim 3, wherein said elastic member comprises a sheetmetal with elasticity, said sheetmetal with elasticity comprises a disc shape.

5. The adjustable orthodontic bracket according to claim 3, wherein said elastic member comprises a sheetmetal with elasticity, said sheetmetal with elasticity has a plurality of slits.

6. The adjustable orthodontic bracket according to claim 3, wherein said elastic member comprises a rubber sheet.

7. The adjustable orthodontic bracket according to claim 3, wherein said orthodontic arch wire fixing member comprises one or more than one orthodontic arch wire slots and fixing wings.

8. The adjustable orthodontic bracket according to claim 3, wherein said orthodontic arch wire fixing member comprises one or more than one orthodontic arch wire fixing tubes.

* * * * *